US008518442B2

(12) United States Patent
Aiache et al.

(10) Patent No.: US 8,518,442 B2
(45) Date of Patent: *Aug. 27, 2013

(54) PROLONGED RELEASE BIOADHESIVE THERAPEUTIC SYSTEMS

(75) Inventors: Jean-Marc Aiache, Paris (FR); Dominique Costantini, Paris (FR); Christine Chaumont, Paris (FR)

(73) Assignee: BioAlliance Pharma, S.A., Paris (FR)

( * ) Notice: Subject to any disclaimer, the term of this patent is extended or adjusted under 35 U.S.C. 154(b) by 121 days.

This patent is subject to a terminal disclaimer.

(21) Appl. No.: 12/830,090

(22) Filed: Jul. 2, 2010

(65) Prior Publication Data

US 2011/0039800 A1    Feb. 17, 2011

Related U.S. Application Data

(63) Continuation of application No. 11/715,967, filed on Mar. 9, 2007, now abandoned, which is a continuation of application No. 11/113,072, filed on Apr. 25, 2005, now Pat. No. 7,651,698, which is a continuation of application No. 10/307,938, filed on Dec. 3, 2002, now Pat. No. 6,916,485, which is a continuation of application No. PCT/FR02/02635, filed on Jul. 23, 2002.

(30) Foreign Application Priority Data

Jul. 23, 2001   (FR) ...................................... 01 09811

(51) Int. Cl.
A61K 47/00         (2006.01)
(52) U.S. Cl.
USPC ............ 424/464; 424/422; 424/434; 424/435
(58) Field of Classification Search
USPC ......................................................... 424/435
See application file for complete search history.

(56) References Cited

U.S. PATENT DOCUMENTS

| | | | |
|---|---|---|---|
| 4,724,141 A | 2/1988 | Schmidt et al. | |
| 4,792,452 A | 12/1988 | Howard et al. | |
| 4,849,229 A | 7/1989 | Gaylord et al. | |
| 4,873,080 A | 10/1989 | Bricki et al. | |
| 4,915,948 A * | 4/1990 | Gallopo et al. | 424/435 |
| 5,116,603 A | 5/1992 | Friedman et al. | |
| 5,160,737 A | 11/1992 | Friedman et al. | |
| 5,330,746 A | 7/1994 | Friedman et al. | |
| 5,362,498 A * | 11/1994 | Aiache | 424/435 |
| 5,955,502 A | 9/1999 | Hansen et al. | |
| 5,985,319 A | 11/1999 | Embil et al. | |
| 6,303,147 B1 | 10/2001 | Gilis | |
| 6,916,485 B2 | 7/2005 | Aiache et al. | |
| 7,651,698 B2 | 1/2010 | Aiache et al. | |

FOREIGN PATENT DOCUMENTS

| EP | 0 095 944 A2 | 12/1983 |
|---|---|---|
| EP | 0542824 B1 | 8/1995 |
| WO | 97/16174 A1 | 5/1997 |
| WO | WO 97/15296 | 5/1997 |
| WO | WO 98/47499 A1 | 10/1998 |
| WO | WO 00/16751 A1 | 3/2000 |

OTHER PUBLICATIONS

Bouckaert et al., 1992, "Comparison of Salivary Miconazole Concentrations After Administration of a Bioadhesive Slow-Release Buccal Tablet and an Oral Gel," *Eur J Clin Pharmacol.* 43(2):137-40.
Final Office Action mailed Oct. 24, 2011 for U.S. Appl. No. 11/715,967.
Non-Final Office Action mailed Feb. 16, 2011 for U.S. Appl. No. 11/715,967.
Office Action mailed Sep. 29, 2009 in Japanese counterpart application JP 2003-515193 (English language translation only).
Response to Office Action mailed Sep. 29, 2009 in Japanese counterpart application JP 2003-515193 filed with the Japanese Patent Office on Mar. 25, 2010 (English language translation only).
PCT International Search Report from PCT/FR02/02635 dated Nov. 19, 2002.
Summary of TIBOZOLE product Characteristics from Tibotec Pharmaceuticals (Revision dated Feb. 2008).
C. Hermant et al., "In vitro fungicidal activity of main antiseptic solutions used as mouthwash against gingival fungal strains in HIV infected patients" Med. Mal. Infect., vol. 27, pp. 715-718 (1997).
D. Greenspan et al., "HIV-related oral disease", Lancet, vol. 348, pp. 729-733 (1996).
F. C. Odds, "Persistence of Miconazole in Saliva after a Single Oral Dose", Clinical Research Reviews, vol. 1, pp. 231-232 (1981).
J. A. Kovacs et al., "Prophylaxis Against Opportunistic Infections in Patients with Human Immunodeficiency Virus Infection", The New England Journal of Medicine, pp. 1416-1429 (May 11, 2000).
J. Vasquez, "Options for the Management of Mucosal Candidiasis in Patients with AIDS and HIV Infection", Pharmacotherapy, vol. 19(1), pp. 76-87 (1999).
JE Clarkson, "Interventions for preventing oral mucositis or oral candidiasis for patients with cancer receiving chemotherapy (excluding head and neck cancer)", Cochrane Database Syst. Rev (2):CD000978 (2000).
M. Weinert et al., "Oral Manifestations of HIV Infection", Annals of Internal Medicine, vol. 125, pp. 485-496 (1996).
N. Imam et al., "Hierarchical Pattern of Mucosal Candida Infections in HIV-Seropositive Women", The American Journal of Medicine, vol. 89, pp. 142-146 (1990).
R. V. Martin-Algarra et al., "Effects of Surfactants on Aminodarone Intestinal Absorption. I. Sodium Laurylsulfate", Pharmaceutical Research, vol. 11(7), pp. 1042-1047 (1994).
Levy et al., 1963, "Effect of Certain Tablet Formulation Factors on Dissolution Rate of the Active Ingredient III", *J. of Pharmaceutical Sciences* 52(12):1139-1144.

* cited by examiner

*Primary Examiner* — Jake Vu
(74) *Attorney, Agent, or Firm* — Dechert LLP

(57) ABSTRACT

The present invention concerns a prolonged release bioadhesive mucosal therapeutic system containing at least one active principle, with an active principle dissolution test of more than 70% over 8 hours and to a method for its preparation. Said bioadhesive therapeutic system comprises quantities of natural proteins representing at least 50% by weight of active principle and at least 20% by weight of said tablet, between 10% and 20% of a hydrophilic polymer, and compression excipients, and comprising between 4% and 10% of an alkali metal alkylsulphate to reinforce the local availability of active principle and between 0.1% and 1% of a monohydrate sugar.

28 Claims, 5 Drawing Sheets

PROLONGED RELEASE BIOADHESIVE THERAPEUTIC SYSTEMS

This application is a Continuation of co-pending Application No. 11/715,967 filed on Mar. 9, 2007, which is a continuation of Application No. 11/113,072 filed on Apr. 25, 2005 (now US Pat. No. 7,651,698 B2 issued on Jan. 26, 2010), which is a continuation of Application No. 10/307,938 filed on Dec. 3, 2002 (now US Pat. No. 6,916,485 issued on Jul. 12, 2005), which is a continuation of Application No. PCT/FR02/02635 filed on Jul. 23, 2002, and for which priority of all the aforementioned applications is claimed under 35 U.S.C. §120; and this application claims priority of Application No. 0109811 filed in France on Jul. 23, 2001, under 35 U.S.C. §119; the entire contents of all are hereby incorporated by reference.

The present invention relates to the medical field, in particular the field of mucosal infections. More particularly, the present invention relates to novel prolonged release bioadhesive therapeutic systems for treating local mucosal infections or the mucitis and candidiasis type. The invention also relates to methods for treating such symptoms and to novel release forms for improving their efficacy. The bioadhesive therapeutic systems of the invention can be used for curative or preventative treatment of such disease types.

Candidiasis is a disease resulting from a local proliferation of fungal species (Candida). Such proliferation can have a number of origins, in particular a local physico-chemical imbalance (modification of pH, etc) associated, for example, with taking antibiotics, steroids or other physical treatments (irradiation, chemotherapy, immunodepressors, etc.). The increase in immunodepression situations (related to immunodepression consecutive upon chemotherapy in the treatment of cancer or the AIDS epidemic) was the cause of a re-emergence of oral candidiasis and severe parodontal disease (Hermant et al., 1997, Med. Mal. Infect. 27: 715-718). Buccal candidiases are routinely detected even in HIV seropositive subjects who are apparently in good health. They are often the first manifestation of an HIV infection. More than 90% of patients with AIDS develop oral candidiasis (Vasquez, 1999, Pharmacotherapy, 19 (1): 76-87). The prevalence approaches 20% in certain populations; it increases with the reduction in the number of CD4 (Greenspan & Greenspan, 1996, Lancet 348: 729-733). Further, candidosa is a common characteristic of infection by the immunodeficiency virus HIV and cancer. The fungal species responsible for those candidiases are *Candida* such as *C. albicans, C. glabrata, C. tropicalis* or *C. krusei*.

Particular signs associated with candidiasis are dry mouth, pain on ingestion, loss of taste, burns, etc. A change in the condition of the buccal cavity has serious implications for the general condition of the patient. Buccal infections that are poorly treated can be the cause of odynophagia and dysphagia, can interfere with speech, mastication and deglutition. Further, the pain caused by those infections leads patients to reduce their food intake; this results in a loss of weight, dehydration and malnutrition. Prevention and treatment of oral candidiasis is thus an essential concern in maintaining quality of life and in preventing more severe complications in those patients (Weinert et al., 1996, Arm Intern. Med. 125: 485-496).

Candidiasis is also a frequent complication in anticancer treatments. In particular, chemotherapy, bone marrow graftings or local irradiation are all factors encouraging the development of local candidiasis type infections. The secondary oral effects of chemotherapy are a major source of morbidity in cancerology. Out of 27 clinical tests: 14 with mucitis (945 randomized cases) and 15 with oral candidiasis (1164 randomized cases), the incidence of mucitis was 50% to 80% and that of candidiasis was 30% to 70% and varied as a function of the location of the cancer. In view of that analysis, partially absorbed treatments appear to be more effective than those which are totally absorbed by the intestinal tract as regards prophylaxis (Clarkson et al., 2000, Cochrane Database Syst Rev. (2): CD000978).

More generally, a further factor encouraging the development of candidiasis is an alteration in the integrity of the mucosa, for example by local or diffuse desquamation. Mucitis is one of such conditions: it involves an erythema generally followed by local desquamation. The alteration in the mucosa (generally buccal) that is induced is the early stage forming the bed of infection, in particular a fungal infection in AIDS or cancer (chemotherapy, bone marrow grafting, local irradiation with tumours to the head and neck, etc). Patients suffer locally from salivary hypofunction, which itself is responsible for an alteration in dental hygiene (Greenspan et al., The Lancet 348 (1996) 729).

Candidosa infections are currently treated in the first intention in a local manner, essentially using antifungals: magistral preparations, lozenges, mouthwashes, azoles, polyenes (Greenspan et al., Lancet 348: 729-733). Azole derivatives are proposed in the second intention, by systemic route, in the case of oesophageal candidiasis (ketoconazole, fluconazole, itraconazole). Such treatments are effective in prevention but are risky (interactions with drugs, resistance, intolerance). Such systemic azoles are reserved for short therapies in confirmed candidiasis (Kovacs et al., 2000, The New England Journal of Medicine, May 11, 1416-1429).

A further disadvantage of these treatments resides in frequently observed relapses. Some studies observed 60% recurrence in the three months following treatment (Imam et al., Amer. J. of Medicine 89 (1990) 142).

Considering the physiopathology of candidiasis, *Candida albicans* and also *C. krusei, C. tropicalis* and *C. glabrata* are the agents responsible for the local infection (mouth, oesophagus, skin, nails, vagina). It can be more or less profound depending on the host's defenses. It is a cutaneo-mucous affection that can induce complications and become systemic. Effective local treatment or preventing buccal candidiasis can avoid systemic candidiasis and the appearance of resistant strains.

Adhesion of the fungus to the mucosa is an essential element in its pathogenicity. The residency time of an antifungal product in the buccal cavity can be an essential element in its immediate and long term efficacy.

Described or existing formulations or compositions are based on forms for systemic administration both as regards their galenic form and the active principles involved.

The present invention provides a prolonged release bioadhesive therapeutic system that is essential for producing a long residence time in the locations of the infection in contrast to the usual local forms (mouthwashes, gel, pastils, lozenges) which have a transitional effect.

By way of example, a buccal gel for local application based on miconazole is sold by Janssen-cilag (92787 Issy-les-Moulineaux, France) under the trade name Daktarin buccal gel® for the treatment of mycoses of the buccal cavity. Miconazole is an antifungal from the imidazole family. It acts in situ after application. As it is only very slightly re-absorbed, it is well tolerated. The dosage for treating buccal mycoses in adult is 125 mg of miconazole (two spoonfuls) applied 4 times a day for 7 to 15 days. The salivary concentration of the miconazole is a good reflection of the efficacy of the product. It varies from 5 to 0.4 µg/ml 30 minutes to 3 hours after applying the gel. Its very rapid reduction is explained by the very short residency time of gel in the buccal cavity. Further, the MIC (minimum inhibitory concentration) of miconazole against *Candidosa albicans* is in the range 1 to 10 µg/ml (Daktarin monograph, medical information from the Swiss Compendium of Medicinal Products). This concentration is only obtained achieved during the short period following application of the gel. As a result, the antimycotic coverage obtained with the buccal gel is mediocre.

Bioadhesive forms and their preparation method have been described in patent EP-0 542 824 B1. They were designed for systemic passage and cannot be used for local action. They do not permit satisfactory in vitro dissolution, a criterion for determining local availability. Thus, they are incompatible with using an active principle such as an antifungal which necessitates local action and/or limited systemic passage.

The present invention aims to overcome all of the disadvantages described above by providing novel prolonged release bioadhesive therapeutic systems by ensuring solubilisation of active principles to ensure its local efficacy. Indeed, prolonged release forms can reduce the number of doses and produce more stable levels of active principle over time.

Throughout the text, the terms "bioadhesive" or "mucoadhesive" will be used equally, therapeutic systems of the invention are more particularly suitable for mucosal administration.

Similarly, the term "therapeutic" encompasses both therapy and prophylaxis of the different pathologies mentioned above, and in particular mucitis and candidiasis.

The bioadhesive therapeutic systems can be in the form of bioadhesive tablets, microspheres or nanospheres.

The present invention also provides a method for preparing said bioadhesive therapeutic systems in the form of tablets with the desired qualities for use on all types of mucosa.

More precisely, the bioadhesive tablets and methods of the invention are suitable for treating mucitis and candidiasis in the context of diseases in immunodepressed subjects (elderly, malnourished, antibiotherapy, cancer, AIDS, radiotherapy, chemotherapy, grafting).

Said tablets are also suitable for administering active principles for which mucosal administration has advantages as regards therapy or comfort, compared with buccal, transdermal or systemic administration. As an example, it may be antivirals such as aciclovir, valaciclovir, ganciclovir, zidovudine or insoluble analgesics such as fentanyl base.

They enable favorable local use of insoluble or slightly soluble active principles. They also enable a number of active principles to be combined in the tablet to increase compliance and acceptability of the treatment, such as other antifungals with a different spectrum, analgesics, salivation agents, etc.

The tablets of the invention also enable that the dose can be reduced and thus, undesirable secondary effects which can accompany the normal use of such drugs can also be reduced. Further, the invention also describes compositions that are particularly advantageous clinically as they are active on the basis of a single (or two) daily dose(s). Finally, their novel formulation does not alter taste and appetite, which are essential elements in maintaining a good general condition in the immunodepressed patient.

The present invention also provides a solution to the disadvantages of the prior art, enabling a more complete and better tolerated control of mucosal infections and associated symptoms (continuous and non-transient cover) and of certain viral diseases, pain or other diseases.

In a first aspect, the invention provides a prolonged release bioadhesive mucosal therapeutic system containing at least one active principle, having an active principle dissolution test of more than 70% over 8 hours, comprising quantities of natural proteins representing at least 50% by weight of active principle and at least 20% by weight of said bioadhesive therapeutic system, between 10% and 20% of a hydrophilic polymer, compression excipients to reinforce the hardness of the bioadhesive therapeutic system, and comprising between 4% and 10% of an alkali metal alkylsulphate and optionally between 0.1% and 1% of a monohydrate sugar.

A particular embodiment of the mucosal bioadhesive therapeutic system of the invention is constituted by a mucoadhesive tablet.

The essential role of adding an alkali metal alkylsulphate is to dissolve a low solubility or insoluble active principle and to facilitate its local availability: the alkali metal alkylsulphate agent facilitates systemic passage of the active principle as a function of its concentration (Martin-Algarra, 1994, Pharmaceutical Research, (11), 7: 1042-1047). In the formulation of the present invention, by forming micelles, it acts as a solubilizing agent that does not facilitate absorption. It also facilitates swelling and allows constant release of the active principle over 8 hours.

More particularly, the bioadhesive therapeutic systems of the invention are suitable for preventing or treating buccal, oesophageal or vaginal infections.

Still more particularly, they are suitable for preventing or treating buccal candidosal infections in immunodepressed patients. The tablets of the invention can be used in a curative or preventative manner. Further, the tablets of the invention are more particularly intended for buccal administration but are also suitable for other forms of administration by adapting the galenic form.

In summary, the bioadhesive therapeutic systems of the invention have a number of major properties and advantages:
- a formulation that allows ready dosage (compatible with preventative or maintenance treatment) and optimum activity of the active principles;
- one or more other active principles and/or excipients can be associated with the first active principle to ensure hydration and good local acceptance of the compositions;
- a dose of active principle that is substantially lower than that used in other existing galenical forms can reduce or avoid undesirable effects;
- the salivary concentrations of active principle are higher than the minimum inhibitory concentration (MIC) over a prolonged period.

The bioadhesive therapeutic systems of the invention contain at least one active principle.

When the bioadhesive therapeutic systems are intended to prevent and treat fungal infections, a preferred active principle is a compound from the broad spectrum azole family preferably selected from miconazole, clotrimazole, ketoconazole, fluconazole, itraconazole, isoconazole, econazole, saperconazole, genaconazole, terconazole, butoconazole, tioconazole, oxiconazole, bifonazole, fenticonazole, omoconazole, sertaconazole, voriconazole and sulconazole. It is advantageously triazoles such as fluconazole, itraconazole or saperconazole; or imidazoles preferably selected from miconazole, clotrimazole and ketoconazole.

Particularly preferred azole compounds in the present invention are miconazole, ketoconazole and itraconazole, and unitary doses are then in the range 10 to 150 mg per tablet.

A still more preferred compound is miconazole whose chemical denomination is (RS)-1-[-2-(2,4-dichlorobenzyloxy)-2-(2,4-dichlorophenyl)-ethyl]-1H-imidazole, present in a dose of 10 to 150 mg per tablet, preferably 25 to 75 mg and more preferably 50 mg per tablet.

Azole compounds are known to act on the synthesis of a constituent of the fungal membrane: ergosterol.

The bioadhesive therapeutic systems of the invention and containing substantially 50 mg per tablet ensure a continuous and prolonged presence of the active principle above the MIC at the site of action in a single daily dose as well as the various advantages described above, and in the absence of systemic passage.

A further advantage of bioadhesive therapeutic systems essentially comprising 50 mg of miconazole is the excellent tolerance of the active principle as the useful dose per day in the 50 mg preparation is ten times lower than the usual dose of the same product in the reference formulation. Daktarin buccal gel formulation (500 mg/d) while surprisingly, the local concentrations are considerably increased (7 to 10). An important advantage is the reduction in the risk of acquiring resistance to the fungi. Indeed, the appearance of resistance to a compound often occurs if the local concentration is less than the MIC allowing the yeast to grow again. The useful dose in the tablets of the invention can also reduce or even eliminate certain undesirable effects resulting from a dose of 500 mg/d, such as intestinal problems (nausea, vomiting, diarrhea) or allergic reactions. Transaminase elevations are rarely observed.

The various advantages of the bioadhesive therapeutic systems of the invention will become clear from the following examples that essentially described the pharmaceutical forms and the results of comparative clinical tests.

The azole miconazole type compound can be associated with a further active principle selected, for example, from an antifungal with a different spectrum, of the polyene type, an analgesic, a salivation agent, a saliva substitute, an antiseptic, an anti-inflammatory (corticoid), thalidomide or a mixture thereof.

Polyenes have a different action mechanism to azoles. They bond to sterol groups, principally ergosterol, present in the fungal membrane and induce the appearance of pores and channels. These pores and channels substantially increase cell permeability and the loss of small molecules, leading to cell death.

From polyenes, preferred polyenes for use in the compositions of the invention are broad spectrum polyenes, preferably tetraenes. Nystatin and amphotericin B can in particular be cited.

Advantageously, nystatin is used in the bioadhesive therapeutic systems of the invention.

Polyenes are advantageously used in doses in the range 10 to 100 mg, preferably in the range 20 to 90 mg. By way of illustration, amphotericin is advantageously used in doses in the range 20 to 60 mg. Nystatin is used in an amount of 10 mg to 100 mg, preferably 20 mg to 40 mg, more preferably about 25 mg.

The doses can be recommended in units knowing that 1 mg corresponds to 4400 units. A preferred composition of the invention comprises 50 to 400 mg of an imidazole or triazole compound and 20 to 90 mg or 100 000 to 200 000 units of a polyene. More preferably, the azole compound is miconazole and the polyene is nystatin. The compositions of the invention are generally intended for use in one or two daily doses. Preferably, they are administered at intervals that allow them to be taken daily in amounts of 20 to 200 mg of azole and 50 000 to 500 000 units of polyene (10 to 110 mg).

Further, to improve the treatment efficacy, the bioadhesive therapeutic systems of the invention applied to mucosal administration can also comprise one or more other active principles. More particularly, the bioadhesive therapeutic systems of the invention can comprise one or more active principles that ensure hydration and local acceptance, an indication of compliance in this type of treatment. The use of this type of active principle is particularly advantageous in acute application and in maintenance treatment.

The associated excipients and other active principles can, for example, advantageously be selected from one or more anaesthetic compounds, salivation agents, antiseptics, anti-inflammatories, thalidomide, antibiotics, saliva substitutes or flavour masking agents, used alone or in combination.

The combined use of an active principle with anaesthetic properties is particularly advantageous since, as indicated above, candidiasis is often accompanied by severe pain, in particular during ingestion. An example of a suitable anaesthetic for use in the context of the invention is lidocaine or tetracaine. Preferably, the anaesthetic is used in doses in the range 0.1% to 10% of the total weight of the active ingredients of the compositions of the invention, more preferably in the range 1% to 7%.

A typical composition in accordance with the invention comprises about 1% to 5% of anaesthetic, for example lidocaine.

The combined use of an agent facilitating salivation is also advantageous for treating candidiasis, which frequently causes dry mouth. In a further aspect, then, the invention concerns a bioadhesive therapeutic system or a composition comprising at least one active principle and a salivation agent.

The active principle can be an antifungal compound as described below, an antiviral for the treatment of HIV infections (human immunodeficiency virus), EBV (Epstein-Barr virus, infectious mononucleosis, hairy leukoplakia), CMV (cytomegalovirus), herpes simplex virus (HSV) or the varicella zoster virus (VZV). The active principles contained in the bioadhesive therapeutic systems are then zidovudine, aciclovir, valaciclovir or ganciclovir. It can also be an insoluble or only slightly soluble analgesic for which other administration modes pose precisely those solubility problems. An example that can be cited is low solubility fentanyl base which is important in treating severe resistant pain in particular associated with cancer.

An example of a suitable salivation agent for use in the context of the invention is pilocarpine. Pilocarpine is currently used in treating xerostomia in patients receiving irradiation when treating cancers of the head and neck. An example of another salivation agent is bethanechol.

The salivation agent is preferably used in doses in the range 0.1% to 10% by weight of the total weight of the active constituents in the compositions of the invention, more preferably between 0.1% and 5%.

A composition of the type defined in the invention comprises about 0.5% to 3% of a salivation agent, for example pilocarpine.

More preferably, a particular association of the invention comprises at least one antifungal compound, an anaesthetic and a salivation agent. More preferably, an advantageous composition of the invention comprises:

25 to 75 mg of an imidazole or triazole compound;
1% to 7% by weight of an anaesthetic; and
0.1% to 5% by weight of a salivation agent.

Further, to improve observance of the treatment, a flavour masking agent can be used if necessary, for example with antifungals. However, in a dose of 50 mg of miconazole, the bioadhesive tablet is characterized by an absence of disagreeable flavour. This agent is preferably free of sugar to avoid possible complications in the mouth, in particular dental problems (caries). In a further embodiment, the bioadhesive therapeutic systems of the invention comprise at least one antifungal compound and a flavour masking agent. This latter comprises mentholated type derivatives, for example. The flavour masking agent is advantageously used in combination with the anaesthetic and the salivation agent as described above.

Further, as indicated above, the combined use of an antiseptic also has major advantages, in particular when used in prophylactic treatment or for maintenance treatment. The use of this type of compound can ensure better oral hygiene for patients afflicted with candidiasis infections. In particular, the use of this type of agent can reduce the bacterial populations present in the oral cavity. A suitable antiseptic is either the alkali metal alkylsulphate alone, or associated with chlorexidine (0 to 5%), an antibiotic (fusafungin, 500 mg, for example) or with an anti-inflammatory, or with a corticoid.

The combined use of said symptomatic active principles endows the compositions of the invention with supplementary properties, in particular:
hydration of the mucosa and mouth;
masked flavour;
comfort in use (controlling pain);
better oral hygiene.

Thus, the present invention shows that it is possible to combine in the active compositions different agents with complementary properties, ensuring more effective treatment of candidiasis infections in patients. In particular, the compositions of the invention allow global treatment of these diseases, in contrast to early or local systemic treatments using azoles, the efficacy of which is high but which can cause resistance.

The active principles used in the context of the invention can be conditioned in the same homogeneous or heterogenous bioadhesive therapeutic system with two phases with two release rates, or separately depending on whether administration is carried out simultaneously or at intervals. Further, they can be formulated in different manners, depending on the nature of the compounds, and the dosage. The formulation can be in the form of homogeneous or double-layer tablets, or in the form of micro- or nano-spheres. In general, packaging and formulation are defined to allow compatibility of the associated products, reduced or facilitated administration frequency (one or two doses a day), easy delivery system (preferably an oral bioadhesive form), a masked taste if necessary, local hydration, an absence of systemic passage and good acceptability.

A further aspect of the bioadhesive therapeutic systems of the invention can be found in the excipients and the fillers. Adhesiveness is conferred by natural proteins, which represent at least 50% by weight of the active principle. Types of natural proteins that can be used are those described in EP 0 542 824. A particular example is a milk protein concentrate titrating a minimum of 85% of proteins such as Prosobel L85, LR85F or, preferably either Promilk 852A sold by Armor Proteinés, or from the Alaplex range (4850, 1180, 1380 or 1395) from NZMP. The relative concentration of the natural proteins in a bioadhesive tablet of the invention is 15% to 50%, preferably 20% to 30%.

The bioadhesive therapeutic systems of the invention also comprise excipients which are normal in bioadhesive systems, as will be shown in the examples below.

A particular characteristic of the compounds of the invention is that they contain between 3.5% and 10% of a metal alkylsulphate. Preferably, it is selected from the group formed by sodium laurylsulphate and diethylsulphosuccinate. More preferably, it is sodium laurylsulphate in a concentration of 4% to 6% by weight of the total tablet weight.

The presence of a dose of more than 3.5% of an alkali metal alkylsulphate and more particularly sodium laurylsulphate can, as will be shown in the following examples, increase the release of miconazole from the tablet in vitro, namely more than 80% over 8 hours as opposed to the active principle being impossible to dissolve in the absence of alkali metal alkylsulphate including over short periods. Thus, it increases the solubility of insoluble or low solubility active principles. This is essential to food availability of the active principle locally. Further, it allows better swelling of the tablet, which has the advantage of producing a constant release of the active principle into the site of action of pathogenic agents. It should be noted that such a concentration of sodium laurylsulphate associated with the adhesive tablet is completely unusual for a tablet in which the concentration of this product rarely exceeds 3%.

Thus in the present invention, the solubilizing function of the sodium laurylsulphate as regards a low solubility active principle has an essential role for its in situ liberation. The examples below indicate good coherence between the in vitro dissolution test and the cumulative salivary concentration over time measured in vivo.

Thus, the presence of sodium laurylsulphate in a concentration of 4% to 6% is an essential element in the composition of tablet and in the qualities of tablet cited above: good availability, a single dose per day, etc.

Sodium laurylsulphate in the minimum concentration of 3.5%, and preferably in the range 3.5% to 10%, also has the advantage of having antiseptic properties per se. Thus, it not only acts as an excipient, but it also acts as an active principle, in particular when treating mucitis.

Finally, the bioadhesive therapeutic systems of the invention can comprise between 0.1% and 1% of a sugar monohydrate, preferably lactose monohydrate or saccharose. The presence of lactose is not, a priori, indispensable per se, provided that the concentration of milk proteins is high. However, the presence of lactose monohydrate or saccharose results in a substantial modification of a step of the preparation process as described in EP 0 542 824-B1, which consists of eliminating a granulation step in the presence of alcohol and replacing it with a wetting liquid composed of lactose or saccharose in purified water, as will be indicated below.

This absence of ethanol has the particular advantage of enabling large scale production of the bioadhesive systems of the invention without using explosion-proof apparatus, which are obligatory when alcohol is present in any step in an industrial process.

The bioadhesive systems of the invention are prolonged release systems and can also be coated with a soluble layer containing the same active principle with immediate release; this is particularly important with analgesic treatments for which a double effect—immediate and prolonged—is sought.

The present invention also concerns a process for preparing a mucosal controled release bioadhesive therapeutic system containing at least one active principle, with an active principle dissolution percentage of more than 70% over 8 hours, comprising at least:
a step for mixing the active principle with natural proteins, these latter representing at least 50% by weight of active principle, and with excipients and fillers comprising at least one hydrophilic polymer; and
a step for mixing with an alkali metal alkylsulphate in a concentration in the range 3.5% to 10% by weight of the bioadhesive therapeutic system, preferably 4% to 6%.

In one implementation, the bioadhesive therapeutic system is a prolonged release mucosal bioadhesive tablet and the preparation of which comprises the following steps:

a) a step for mixing the active principle with natural proteins, said proteins representing at least 50% by weight of the active principle, and with excipients and fillers comprising at least one hydrophilic polymer;
b) a step for wetting the mixture obtained at a) with a monohydrate sugar or polyol type binder;
c) a step for drying the mixture and sizing the grains obtained;
d) a step for mixing the grains obtained with an alkali metal alkylsulphate in a concentration in the range 3.5% to 10% by weight of tablet, preferably 4% to 6%.

In the method of the invention, the active principle or active principles, if necessary mixed with methylhydroxypropylcellulose or metolose (MHPC) is sieved with an open space of between 0.4 and 1 mm, then mixed with at least 50% by weight of natural proteins, such as milk proteins. The powder obtained is homogenized. It then undergoes wetting step in a granulation step in which the powder is mixed with a lactose or saccharose solution in distilled water. It is then followed by drying to produce a residual moisture content of about 3%. It is then followed by a calibration step, mixing with the remaining excipients and by a compression step. A particular feature of the wetting liquid, lactose in water, is that the quantity introduced during batch production is not fixed but should be determined as a function of the appearance of the grain. There are three possibilities:

either all the wetting liquid is introduced and the subsequent production phases of tablet are carried out conventionally by adding excipients, as indicated in the examples below;
or not all of the wetting liquid is used and metolose is added with the formulation excipients to arrive at a final concentration (between 0.1% and 1%, preferably between 2% and 4% of the final tablet). A typical production diagram is shown in FIG. 1 illustrating Example 2;
or all of the lactose or saccharose is dissolved in half of the theoretical quantity of purified water. All of this wetting liquid is introduced into the mixture. The remaining half of the purified water is used as a reserve when optimizing wetting and can be adjusted as a function of batch size.

This latter possibility avoids the phase for compensating for the monohydrated lactose with metolose. It is particularly advantageous when scaling up as the quantities to be introduced can be calculated by knowing the batch size without a need to known the grain appearance. The scaling up experiments shown below indicate that the method is suitable for large scale production both with lactose and with saccharose. Large scale dissolution tests with the composition of Example 3 demonstrate this.

A further essential characteristic of the method for preparing tablets of the invention is adding an alkali metal alkylsulphate in step d) above in a concentration in the range 3.5% to 10% of the tablet weight, preferably in the range 4% to 6%. It is actually added at the same time as the formulation excipients such as talc and magnesium stearate, to endow the tablets with the functions described above, in particular as regards rate of dissolution.

The invention also concerns a method for preparing a bioadhesive therapeutic system other than tablets, such as microspheres, in which a step for adding an alkali metal alkylsulphate in the same range of concentration as described above is added to the preparation.

The alkali metal alkylsulpahte is preferably sodium laurylsulphate or sodium diethylsulphosuccinate. The production of pilot batches described in the examples below used sodium laurylsulphate in a concentration of 4.5%.

The method of the invention results in prolonged release bioadhesive tablets that are particularly suitable for application to the mucosa, and more particularly to the buccal mucosa.

The examples pertain to tablets containing as the active principle antifungal substances for treating buccal candidiasis, anti-infectious substances (AZT, aciclovir), active principles for treating pain (fentanyl) or nausea (metoclopramide). The skilled person will be capable of adapting the production of the bioadhesive therapeutic system with a further active principle for application to other types of mucosa and/or for other types of diseases.

For active principles with absorption, two action mechanisms, local and systemic, can be obtained. The following can be cited: aphthae for buccal infections, anti-infectious agents for vaginal infections, inflammation, local antalgics or opioid analgesics for pain, dryness, metoclopramide for nausea, antiulcerous agents and local bacterial infections.

Finally, the present invention concerns the use of bioadhesive therapeutic systems to dissolve active principles and to allow prolonged release as a drug for preventative, curative or maintenance treatment of diseases, in particular of the mucosa. More particularly, the advantage of the bioadhesive therapeutic systems of the invention is their use to prevent or treat candidoza infections of the buccal mucosa and the bioadhesive therapeutic system contains an azole as the active principle in a dose of 10 to 150 mg per tablet preferably 25 to 75 mg per tablet.

For the treatment of other buccal infections, vaginal or global infections and more particularly HIV infections (human immunodeficiency virus), EBV (Epstein-Barr virus, infectious mononucleosis, hairy leukoplakia), CMV (cytomegalovirus), herpes simplex virus (HSV) or varicella zoster virus (VZV), the active principles contained in the bioadhesive therapeutic systems are zidovudine, aciclovir, valaciclovir or ganciclovir. The doses of aciclovir and valaciclovir are 20 to 100 mg, preferably 50 mg. Doses for zidovudine and ganciclovir are 10 to 2000 mg, preferably 500 to 1500 mg. The desired action is local and more particularly, at the place of entry of the infectious agent, but also general because of the particular mode of action of these viruses in ganglionic tropism.

Bioadhesive therapeutic systems can also be used for drugs for treating aphthae or pain. When treating pain, the systemic action is more advantageous, associated with local release, and is achieved with a bioadhesive therapeutic system by dint of its mode of release. The low bioavailability of fentanyl is improved by the bioadhesive form which dissolves and releases the active principle into the buccal mucosa. This bioadhesive system applied to fentanyl can associate an immediate action with a prolonged action that is particularly advantageous in pain and in particular for intense, resistant pain, in particular that associated with cancer.

The bioadhesive system of the invention is particularly advantageous when the active principle is fentanyl base which is an insoluble molecule and the solubility of which is improved with laurylsulphate. A range of doses of fentanyl of 50 to 1600 µg, and preferably 200 to 1200 µg, is possible with this therapeutic system, and can be adapted to the pain to be treated.

The use of the bioadhesive therapeutic systems of the invention is particularly attractive for the patient, since prolonged release allows a single daily administration of the bioadhesive therapeutic system and it permits local mobilization of the active principle and low systemic passage. The various advantages of the bioadhesive therapeutic system and in particular the tablet of the invention prepared using the method described above appear in the examples described below illustrated in the figures.

EXAMPLE 1

Effect of Sodium Laurylsulphate on a Bioadhesive Tablet Dissolution Test

The solubility characteristics of miconazole in a prolonged release adhesive form were tested successively using a dissolution test under conventional formulation conditions as described in EP 0 542 824, under modified conditions but without laurylsulphate then with addition of sodium laurylsulphate to the primary grain under the conditions of Example 2 below and FIG. 1.

1.1. Formula without Sodium Laurylsulphate:

The dissolution test carried out in pure water produced very low miconazole dissolution percentages (<5%) early on (1 h and 3 h).

1.2. Formula without Sodium Laurylsulphate and Changing the Test Conditions:

Because the dissolution test was impossible in pure water and taking into account the recommendation from EMEA (Note for guidance on quality of modified release products), the dissolution test conditions were modified to obtain the most discriminating in vitro test. The test retained still satisfied the demands of the Pharmacopee Europdenne (Essai de dissolution des formes solides, Phée Eur 1997, 2.9.3) and was characterized by a dissolution medium containing 0.05% of sodium laurylsulphate.

1.3. Formula Containing Sodium Laurylsulphate:

After adding 4.5% of sodium laurylsulphate to the miconazole tablet, the dissolution test produced satisfactory results for a prolonged release form.

Comparative results for the dissolution tests for the three formulae are shown in Table I below:

TABLE I

| | Miconazole dissolved (%) | | |
|---|---|---|---|
| Time (h) | Formula 1.1 | Formula 1.2 | Formula 1.3 |
| 1 | <5% | 14.8 | 9.2 |
| 3 | <5% | 35.5 | 35.8 |
| 5 | ND | 52.2 | 61.1 |
| 8 | ND | 73.1 | 85.8 |

In formula 1.2, the dissolution test was improved over formula 1.1, but we can conclude that release of the active principle was insufficient for a prolonged release drug.

Formula 1.3 with sodium laurylsulphate not only allowed prolonged release of miconazole but also produced novel qualities (wetting, swelling and dissolving of the active principle for constant in situ local concentrations).

EXAMPLE 2

Figure 1:
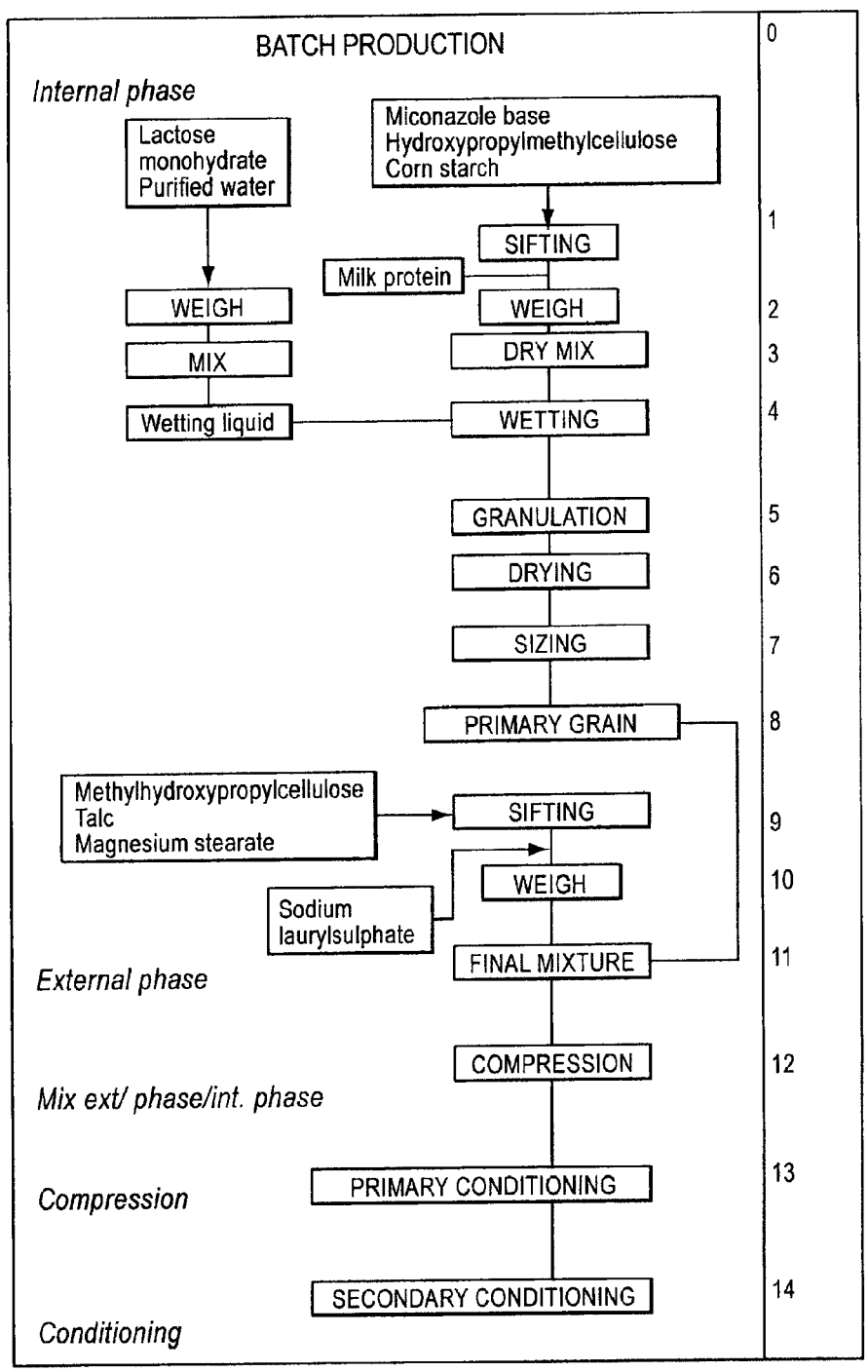
FIG. 1 shows a typical production diagram for a tablet of the invention.

Preparation of a Tablet Containing 50 mg of Miconazole a) 1.9 kg batch:

The preparation diagram for this tablet is shown in FIG. 1. 50 mg of miconazole base (or 100 mg for a 100 mg tablet) was mixed with 9.2 mg of corn starch and 20.5 mg of methylhydroxypropylcellulose.

The mixture was then homogenized by sieving and 27.43 mg of LR85F milk proteins was added and mixed with the initial mixture. This latter was then wetted with a mixture of lactose monohydrate (lactose 200 Mesh in an amount of 0.39 mg in purified water). During batch production, all of the wetting liquid was introduced, namely 0.39 mg per 115 mg tablet, representing 0.34% by weight of the total constituents. The wetting step was followed by a granulation, drying and sizing step carried out under conventional conditions, to obtain the primary grain indicated in FIG. 1.

A mixture of excipients was added to this primary grain: talc, magnesium stearate, methylhydroxypropylcellulose, to which sodium laurylsulphate in a concentration of 4.5% was added after sieving.

The final mixture then underwent conventional phases of tablet compression and packaging.

The composition of a 50 mg dose tablet and that of a 100 mg dose tablet are shown in the table below.

TABLE II

| | composition 1 | | |
|---|---|---|---|
| | 50 mg dose batch Composition in mg/tablet | 100 mg dose batch Composition in mg/tablet | % |
| miconazole base | 50.00 | 100.00 | 43.50 |
| methylhydroxy-propylcellulose Metolose 90SII150000 | 20.50 | 41.00 | 17.80 |
| LR85F milk proteins | 27.43 | 54.86 | 23.80 |
| corn starch | 9.20 | 18.40 | 8.00 |
| lactose monohydrate (lactose 200 Mesh) | 0.39 | 0.78 | 0.34 |
| sodium laurylsulphate | 5.18 | 10.35 | 4.50 |
| magnesium stearate | 1.32 | 2.65 | 1.15 |
| talc | 0.98 | 1.96 | 0.85 |
| purified water | qs | qs | |
| TOTAL | 115.00 | 230.00 | 100 |

In this composition, the milk proteins could be selected from all of the concentrates cited above provided that they titrated at least 85% of proteins.

Further, saccharose could be substituted for lactose under the same conditions as Example 7 below.

b) Scale-up: 10 kg Batch:

Industrial scale-up was carried out respecting the same composition as that in Table II above to produce a 10 kg batch.

On a large scale, the method of FIG. 1 can be adapted and simplified:
- by introducing a fixed quantity of lactose, without compensating with metolose;
- by carrying out a previous calculation of the quantity of water to be introduced, which meant that the grain appearance could be ignored, rendering the method adaptable to closed vessel apparatus.

The dissolution tests carried out on the compositions of Example 3 below indicate the industrial feasibility of the method on a large scale, since the results were no different from those obtained for tablets from the 1.9 kg batch.

EXAMPLE 3

In vitro Dissolution Test a) Comparison of 50 mg and 100 mg/tablet Dosed Tablets:

Release of miconazole from its galenic form and the disintegration rate of the tablet were measured in vitro using a dissolution test. The test was carried out in a paddle apparatus rotating at 60 rpm at 37° C. in a suitable medium, following the recommendations of the Pharmacopee Europeenne. The miconazole was assayed using HPLC technique.

The results obtained for the two types of tablets BA001-50 and BA001-100 are shown in Table III below. Only the percentages of released miconazole are shown in the table; indeed, the disintegration percentages results for the tablet were completely superimposable.

TABLE III

| | dissolved miconazole (%) | |
|---|---|---|
| Time (h) | 50 mg tablet | 100 mg tablet |
| 1 h | 9.2 ± 1.7 | 7.8 ± 0.5 |
| 3 h | 35.8 ± 4.6 | 30.2 ± 1.3 |
| 5 h | 61.1 ± 6.2 | 51.5 ± 2.0 |
| 8 h | 85.8 ± 3.5 | 74.4 ± 1.7 |

These studies show that after 8 hours, almost all of the miconazole has been released from its galenic form for the 50 mg tablet and the release was constant. The results obtained with the 100 mg tablet were of the same order. These release times were long, allowing prolonged release to be envisaged in vivo into the buccal cavity, resulting in a prolonged antifungal effect. This hypothesis was verified by the phase 1 clinical study in the healthy volunteer in Example 4 below. This study was carried out with two doses of miconazole (50 and 100 mg). By examining the respective release times obtained in vitro and the minimum desired salivary concentrations, one of the two doses could be selected and its administration frequency deduced.

b) Comparison of a Laboratory Size Batch and an Industrial Size Batch.

The respective quantities of the products were as follows:

| | quantities (g) | |
|---|---|---|
| 50 mg miconazole tablets row materials | 1.9 kg batch (17 000 tablets) | 9.8 kg batch (85 000 tablets) |
| miconazole base | 850.00 | 4261.00 |
| metolose | 348.5 | 1747.00 |
| milk protein concentrate | 466.31 | 2337.00 |
| corn starch | 156.4 | 784.00 |
| lactose monohydrate | 6.63 | 34.00 |
| sodium laurylsulphate | 88.06 | 441.00 |
| magnesium stearate | 22.44 | 112.70 |
| talc | 16.66 | 83.30 |
| total | 1955.00 | 9800.00 |

Figure 2:
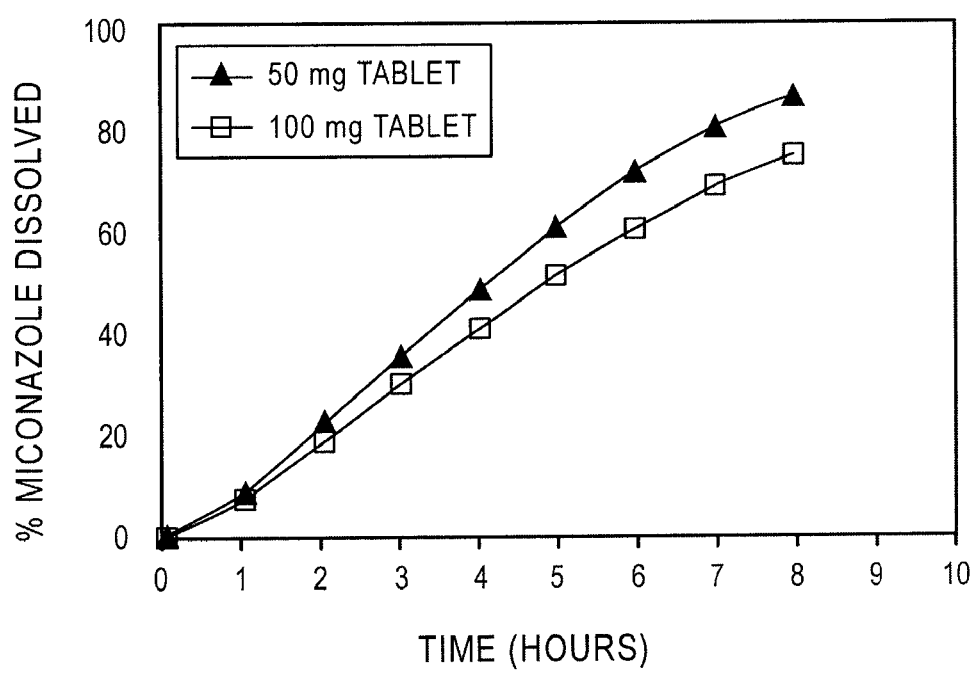
FIG. 2 shows an in vitro dissolution test for a tablet with two different dosages (50 mg and 100 mg) containing sodium laurylsulphate in a concentration of 4.5%.

The dissolution tests obtained for the two batches were similar to those of FIG. 2 with more than 70% dissolution over 8 hours.

EXAMPLE 4

Results of Texturometer Bioadhesion Tests

This test was intended to compare the adhesive properties of tablets in vitro.

Apparatus:

The apparatus used for this test was a texturometer (type TEC 025). It was composed of the following elements:
- a lever arm to allow the probe to be raised and lowered;
- a 200 N force sensor which measured the force necessary to fracture the tablet;
- a disposable plastic probe on which the tablet is fixed;
- a steel module surmounted by a plastic 4 cm diameter crystallizer, the base of which was constituted by a stainless steel plate. This crystallizer will contain the medium necessary for wetting the tablets.

Operating procedure:
- fix tablet to be studied on a plastic probe with cyanoacrylic adhesive;
- screw the probe onto the lever arm of the texturometer;
- place deionized water in the crystallizer (about 4 ml);
- lower the probe into the crystallizer until the tablet is completely immersed and leave the tablet in the water to wet it for a defined period;
- measure the in vitro adhesivity by applying the texturometer protocol which comprises three steps:
  - step 1: lower the probe until the tablet comes into contact with the metal plate;
  - step 2: contact phase, which adheres the tablet to the plate;
  - step 3: lift probe: fracture phase.

In the table below, the probe raising and lowering rates were fixed at 0.25 mm/s, the wetting and contact times were fixed at 60 seconds, and the study medium used was deionized water.

The results were as follows:

| | positive work (J) | |
|---|---|---|
| tests | formula with lactose | formula with saccharose |
| tablet 1 | $4.00 \times 10^{-4}$ | $3.40 \times 10^{-4}$ |
| tablet 2 | $3.78 \times 10^{-4}$ | $3.18 \times 10^{-4}$ |
| tablet 3 | $3.45 \times 10^{-4}$ | $2.93 \times 10^{-4}$ |
| tablet 4 | $4.06 \times 10^{-4}$ | $3.25 \times 10^{-4}$ |
| mean | $3.82 \times 10^{-4}$ | $3.19 \times 10^{-4}$ |
| standard deviation | $0.275 \times 10^{-4}$ | $0.19 \times 10^{-4}$ |

Interpretation of Results:

The data measured by the force sensor were analyzed using Texturometer TEC v6.0 ETIA 1996 software and expressed in the form of a force (N)/time (s) curve. This software could also trace a force/distance (mm) curve. The in vitro adhesivity of tablets was evaluated by the value of the positive work (J) measured during the tablet fracture phase. This work was represented by the area under the force/distance curve.

The higher the value, the better the bioadhesive properties of the tablet.

The results obtained under identical conditions with tablets of the same diameter allowed a comparison between different formulations.

EXAMPLE 5

In vivo Prolonged Release Study with the Tablet of the Invention

This study was carried out by means of a salivary kinetics using 18 healthy volunteers and with two dosages of miconazole (50 and 100 mg). The tolerance of this galenical form was also evaluated.

The tablets of the invention were compared with a buccal gel containing miconazole. Since the gels did not remain in the buccal cavity, they had to be applied several times a day. The maximum salivary concentrations of miconazole were observed immediately after application, but the active principle was rapidly eliminated from the buccal cavity (Odds, 1981, Clean Raise Rev. 1:231-232). After applying 6.25 g of buccal gel, equivalent to 125 mg of miconazole, the salivary concentrations were 5 to 0.4 µg/ml from 30 min to 3 hours following application. The administration frequency was four applications per day.

5.1 Aims of the Study:

Principal aim:

The principal aim of this study was to determine the salivary kinetics of miconazole from two types of prolonged release (PR) tablets, 50 or 100 mg, in eighteen healthy volunteers and to compare them with that obtained with the buccal gel (125 mg of immediate release miconazole) under the same conditions.

Secondary aim:

The secondary aims of this study were as follows:
- to determine the blood pharamokinctics of miconazole from two types of prolonged release (PR) tablets, 50 mg or 100 mg;
- to evaluate the clinical tolerance of bioadhesive miconazole buccal tablets;
- to determine the acceptability and tolerance by the subject him/herself.

5.2 Study Scheme:

A monocentric randomized cross-over phase 1 study in the healthy volunteer. Eighteen subjects each received 3 types of products in a different order with a latency period of 8 days between each administration.

The 3 products administered were the 50 mg bioadhesive miconazole tablet, the 100 mg bioadhesive miconazole tablet and the 125 mg per dose immediate release miconazole gel. The treatments were numbered 1 to 18. In each treatment, the product was blind labeled "week 1", "week 2" or "week 3" (50 mg or 100 mg tablet or gel).

A salivary and sanguine assay of miconazole was effected prior to administering the product. Then, a salivary and blood sample was taken at 30 minutes then 1 hour and then every hour up to 12 hours for the saliva or up to 4 hours for the blood with a blood sample then being taken at 8 and 12 hours; a saliva and a blood sample were taken at 24 hours.

Samples:

Salivary sample: to avoid abnormally high miconazole levels, the tongue could not be in contact with the tablet for the 10 minutes preceding sample removal. Further, for samples removed 30 minutes after an administration, care had to be taken to wash the subject's lips;

2 ml of saliva was collected in a borosilicate tube over a period of 2 min (1 min prior to and 1 min after the given time).

The labeled tubes were preserved at −20° C. to await analysis.

Blood sample: the labeled borosolicate tubes of collected blood were preserved at −20° C. to await analysis.

Means of administration and adhesion of bioadhesive tablets:

Means of administration: the tablet was removed from the unit flask and placed under the upper lip in the canine fossa. It was positioned either with the fingers or with a disposable device that could centre the tablet in the canine fossa and facilitate its adhesion.

Adhesion period: the adhesion period of tablet was noted. It was defined as the time after which the tablet was no longer visible in the vestibule or on the gum with a sensitive external control carried out at the time of each sample. The circumstances of the end of adhesion had to be specified (erosion or detachment of the tablet). In the case of detachment, the time was noted and the tablet had to be swallowed.

Means for administering the buccal gel (in accordance with Daktarin® 2% buccal gel notice):

The dosage was 2 spoonfuls as provided with the tube of gel. The gel had to be kept in the mouth for as long as possible (2 to 3 minutes) before swallowing it. Administration had to be carried out between meals or drinks or at least 10 minutes afterwards.

Buccal examination:

This was carried out after 10 h by the same person who carried it out prior to administering the product.

5.3 Evaluation:

a) Principal Evaluation Criterion:

Salivary pharmacokinetics of miconazole:

Miconazole was assayed blind using high performance liquid chromatography technique. The results are expressed using the normal pharmacokinetic criteria ($C_{max}$, $T_{max}$, AUC) and the products were compared. The results are shown in Table IV below.

b) Secondary Criteria:

Blood assay of miconazole:

Miconazole was assayed blind by high performance liquid chromatography technique. The results were expressed using normal pharmacokinetic criteria ($C_{max}$, AUC) and the products were compared.

Local clinical tolerance of bioadhesive tablet:

This was evaluated by a clinical examination of the buccal mucosa carried out by the same investigator 10 hours after administration.

The tolerance was also determined for each product and on the day of each administration by the volunteer himself using a questionnaire (four possible choices: good, acceptable, modest or disagreeable: if disagreeable, details were provided).

Acceptability of bioadhesive tablet:

The volunteer determined this using a questionnaire for each product and the day of each administration (four possible choices: good, acceptable, modest or disagreeable: if disagreeable, details were provided).

Figure 3:
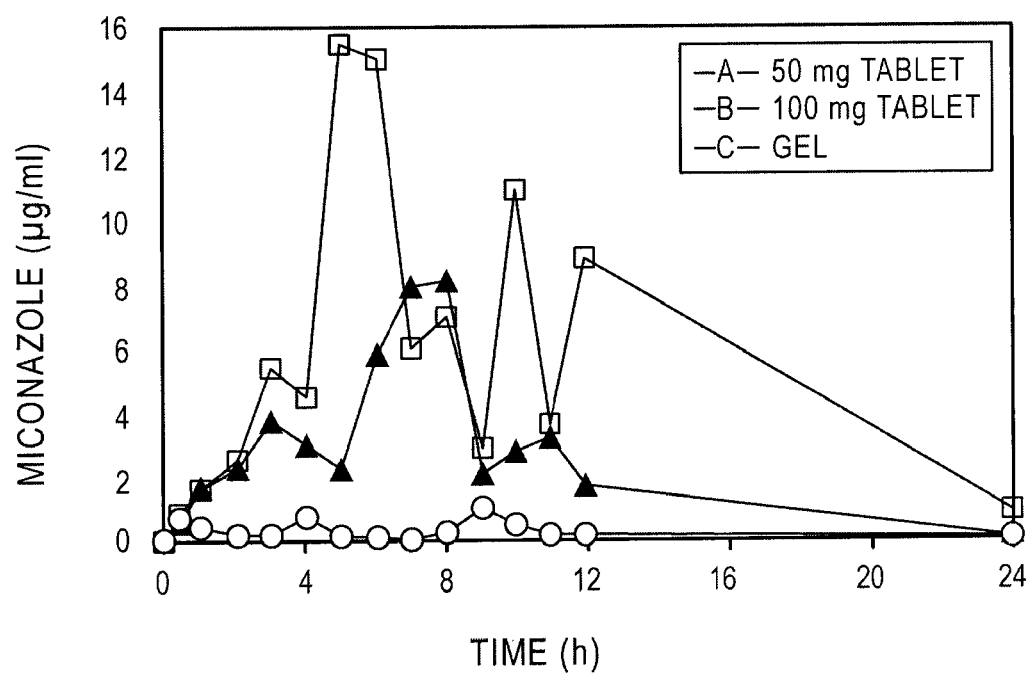
FIG. 3 shows the mean salivary concentration obtained with time for miconazole by comparing a tablet containing 50 mg of miconazole (black triangle), a tablet containing 100 mg of miconazole (white square) and a gel containing miconazole sold under the trade name Daktarin® (white circles).

5.4 Results:

a) Salivary Concentration Obtained In Vivo:

The salivary concentration results obtained over time in vivo are shown in FIG. 3 and Table IV below.

TABLE IV

| treatment | $C_{max}$ (µg/ml) | $T_{max}$* (h) | AUC 0-12 (µgl · h/ml) |
|---|---|---|---|
| 100 mg bioadhesive tablet | 39.06 ± 49.29 | 6 | 78.62 ± 78.42 |
| 50 mg of bioadhesive tablet | 15.07 ± 16.21 | 7 | 42.97 ± 31.99 |
| gel | 1.61 ± 1.62 | 4# | 3.43 ± 4.14 |

*mean;
corresponds to 0.5 hours after second administration.

These results show that the 50 mg dose tablet had a maximum salivary concentration of 15.07 µg/ml while it was 1.61 µg/ml for the buccal gel. The three peaks observed in FIG. 3 correspond to three administrations of the gel just after T0, T4 and T9 while the tablets were administered just once. It thus appears that the salivary concentration was very substantially higher with the tablets compared with that obtained with the buccal gel.

The MICs (minimum inhibiting concentration) of miconazole for Candidosa albicans are 1 to 10 µg/ml. The salivary concentrations of more than 1 µg/ml show that the gel rarely exceeded this threshold while the 50 mg bioadhesive tablet was regularly above this threshold (16 subjects out of 18 as opposed to 0 with the gel). The mean daily time during which the 50 mg bioadhesive tablet had salivary concentrations of more than 1 µg/ml was 7.22 hours (as opposed to 0.61 hours for the gel). This means that the concentration ensured a sufficient pressure locally on any germs and thus a reduced risk of the appearance of resistant strains.

b) Other Results:

The mean tablet adhesion time was 15 hours for the 50 and 100 mg tablets.

The mean blood concentration was 0.035 µg/ml for the gel, as opposed to 0.020 µg/ml for the 50 mg tablet and 0.013 µg/ml for the 100 mg tablet.

The local and general tolerance was good; the bioadhesive tablets were preferred in 17 cases out of 18 (as opposed to 1 in 18 for the gel).

Flavour proved to be a particularly important criterion in a spontaneous questionnaire regarding the gel (13 cases out of 18 indicated a poor flavour as opposed to 2/18 for the 100 mg tablet and 1/18 for the 50 mg tablet).

EXAMPLE 6

In Vitro/in vivo Correlation

Figure 4:
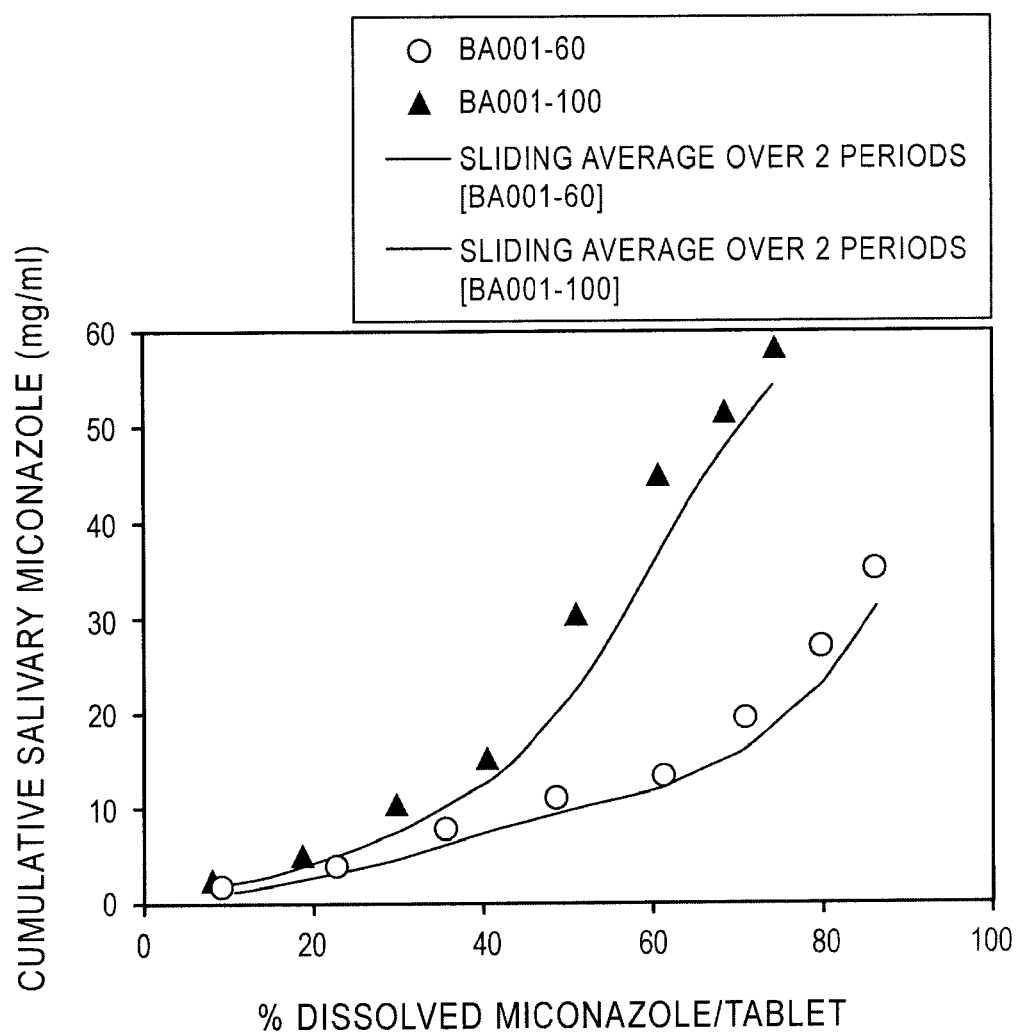
FIG. 4 shows the correlation between the salivary miconazole levels expressed in µg/ml and the percentage dissolution in vitro.
Figure 5:
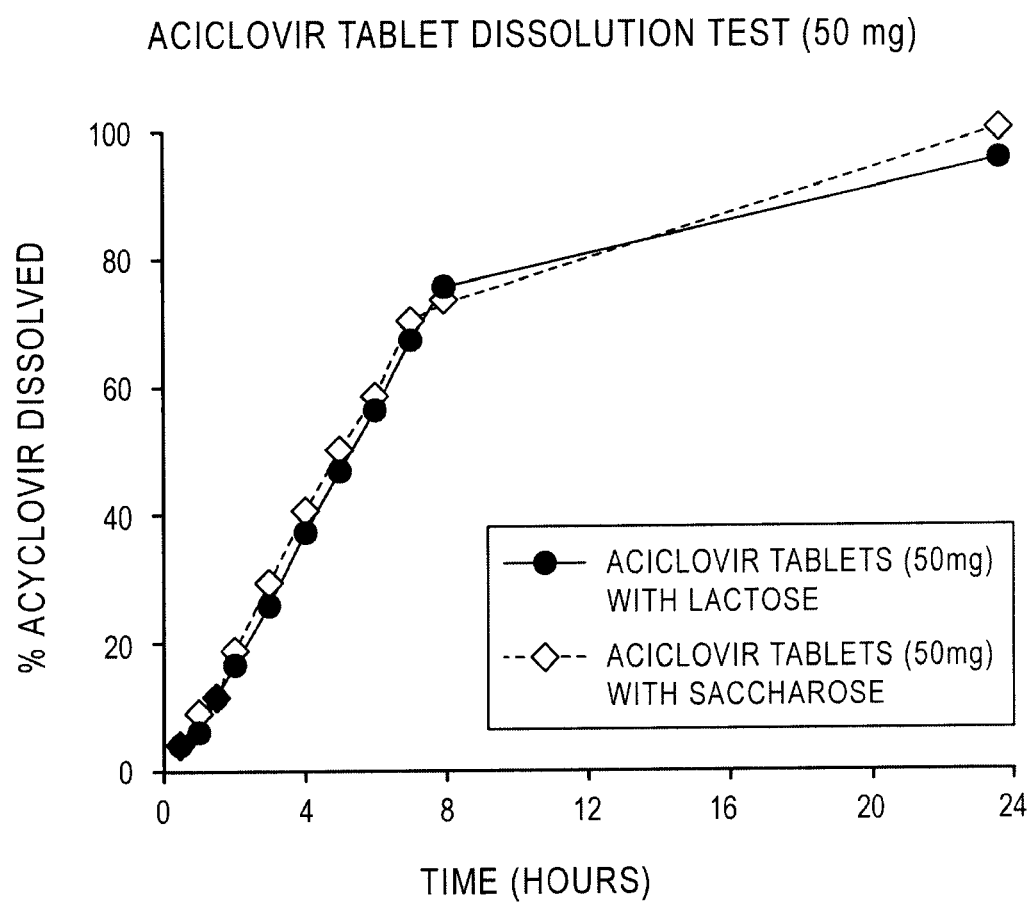
FIG. 5 shows in vitro dissolution tests for 50 mg dose tablets of aciclovir containing sodium laurylsulphate in a concentration of 4.5% and lactose or saccharose as a binder.

FIG. 4 shows the cumulative salivary amounts of miconazole (µg/ml) as a function of the in vitro dissolution test carried out over 8 hours. The in vitro dissolution test is shown along the abscissa in the form of the ratio of the percentage of dissolved miconazole with respect to the percentage of miconazole in the tablet. This figure clearly indicates that everything released from the tablet was found in the saliva. Deglutition was considered to be constant and systemic passage was zero. In the second portion of the curve, in which the slope increased, more miconazole was assayed in the saliva than was released form the tablet.

This result is particularly important. Indeed, the most likely hypothesis that can be proposed to support these results and in the absence of systemic passage is that the active principle is being released from the buccal mucosa. In the first phase, then, deglutition occurs with a loss of active principle, associated with storage of the active principle in the buccal mucosa. This storage can be explained by an equilibrium of the active principle in micelles formed by the laurylsulphate, which can then precipitate out and adhere to the mucosa; it is then released as the saliva is secreted.

Then, the tablets of the present invention have the advantage not only of producing no systemic passage but that the buccal mucosa forms a reservoir for the active principle. This explains the fact that taking 50 mg of active principle once in 24 hours is surprisingly sufficient while Daktarin® buccal gel is administered daily in an amount of 500 mg/day.

EXAMPLE 7

Different Compositions Produced from the Bioadhesive Systems of the Invention 7.1 Modifications to Active Principle:

Composition 1 of Table II in Example 2 was repeated with other active principles under the following conditions:

| composition n° | active principle | concentration mg/tablet | administration method | authorized concentration range |
|---|---|---|---|---|
| 1 | miconazole | 50 | buccal or vaginal | 2-100 |
| 2 | aciclovir | 50 | buccal or vaginal | 2-100 |
| 3 | AZT | 700 | vaginal | 10 to 2000 preferably 500 to 1500 |
| 4 | methoclopramide | 100 | buccal | 20-100 |
| 5 | fentanyl | 1 | buccal | 0.05-1.6 |
| 6 | laurylsulphate | 5.18 | buccal or vaginal | 1-100 |

7.2 Replacing Lactose with Saccharose:

In all of the compositions, the 0.39 g per tablet of lactose could be substituted with 29.59 g±3 of saccharose.

The results for the dissolution tests and adhesivity tests were similar.

7.3 Production of a Rapid and Prolonged Release Tablet:

The above compositions could be coated when the therapy required a rapid release layer of the same active principle.

The geometry of these two layers—rapid release and prolonged release—was not important and could be achieved using any technique that is known to the skilled person provided that the bioadhesive qualities of the tablets of the invention were retained.

CONCLUSION

The present invention provides a preparation method and prolonged release bioadhesive tablets which enable administration of an active principle in an amount of 24 hours in a dose of close to 10 times lower than the reference galenical form proposed now. Further, the dissolution test, namely more than 70% over 8 hours, is adapted to the frequency of administration. In the case of miconazole, not only a low systemic passage is observed but, further, it would appear that the in situ concentrations ensure local antimycosal cover over a prolonged period. The form is adhesive for a prolonged period and is well tolerated, the flavour and acceptability are improved, rendering the invention useful clinically and extrapolatable to many active principles.

More generally, the present invention can be adapted to other mucoadhesive microsphere or nanosphere systems.

The invention claimed is:

1. A prolonged release bioadhesive therapeutic system comprising:
   at least one antifungal agent from the broad spectrum azole family,
   natural proteins representing at least 50% by weight of the antifungal agent and at least 20% by weight of said bioadhesive therapeutic system,
   between 10% and 20% of a hydrophilic polymer, compression excipients, and
   between 3.5% and 10% of an alkali metal alkylsulfate.

2. The bioadhesive therapeutic system according to claim 1, wherein said bioadhesive therapeutic system is a mucoadhesive tablet.

3. The bioadhesive therapeutic system according to claim 2, wherein the alkali metal alkylsulfate is sodium lauryl sulfate or sodium diethyl sulfosuccinate.

4. The bioadhesive therapeutic system according to claim 2, in which the alkali metal alkylsulfate is sodium lauryl sulfate.

5. The bioadhesive therapeutic system according to claim 1, wherein the compression excipients contain corn starch.

6. The bioadhesive therapeutic system according to claim 2, in which the antifungal agent is miconazole present in a dose of 10 to 150 mg per tablet.

7. The bioadhesive therapeutic system according to claim 6, further comprising a second agent selected from: a polyene antifungal agent with a different spectrum than the antifungal agent from the broad spectrum azole family; an analgesic; a salivation agent; an antiseptic; a salivary substitute; an anti-inflammatory agent; an antibiotic; thalidomide; and mixtures thereof.

8. The bioadhesive therapeutic system according to claim 7, in which the second active agent is a polyene in a dose of 10 to 100 mg per tablet.

9. The bioadhesive therapeutic system according to claim 7, further comprising 0.1% to 10% by weight of an anesthetic and/or 0.1% to 10% by weight of a salivation agent.

10. The bioadhesive therapeutic system according to claim 4, in which the sodium lauryl sulfate is present in a concentration of 4% to 6%.

11. The bioadhesive therapeutic system according to claim 1, in which the antifungal agent is selected from miconazole, clotrimazole, ketoconazole, fluconazole, itraconazole, isoconazole, econazole, saperconazole, genaconazole, terconazole, butoconazole, tioconazole, oxiconazole, bifonazole, fenticonazole, omoconazole, sertaconazole, and sulconazole.

12. The bioadhesive therapeutic system according to claim 6, in which the miconazole is present in a dose of 25 to 75 mg per tablet.

13. The bioadhesive therapeutic system according to claim 6, in which the miconazole is present in a dose of 50 mg per tablet.

14. The bioadhesive therapeutic system according to claim 8, in which the polyene is present in a dose of 20 to 90 mg.

15. The bioadhesive therapeutic system according to claim 1, in which the natural proteins are a milk protein concentrate.

16. The bioadhesive therapeutic system according to claim 1, in which the hydrophilic polymer is methylhydroxypropylcellulose or metolose.

17. The bioadhesive therapeutic system according to claim 1, in which
   the antifungal agent is miconazole,
   the natural proteins are a milk protein concentrate,
   the hydrophilic polymer is methylhydroxypropylcellulose or metolose, and
   the alkali metal alkylsulfate is sodium lauryl sulfate.

18. The bioadhesive therapeutic system according to claim 17, in which the miconazole is present in a dose of 10 to 150 mg per tablet.

19. The bioadhesive therapeutic system according to claim 17, in which the miconazole is present in a dose of 25 to 75 mg per tablet.

20. The bioadhesive therapeutic system according to claim 17, in which the miconazole is present in a dose of 50 mg per tablet.

21. The bioadhesive therapeutic system according to claim 17, in which the milk protein concentrate is present in a relative concentration of 15% to 50%.

22. The bioadhesive therapeutic system according to claim 17, in which the milk protein concentrate is present in a relative concentration of 20% to 30%.

23. The bioadhesive therapeutic system according to claim 17, in which the sodium lauryl sulfate is present in a concentration of 4% to 10%.

24. The bioadhesive therapeutic system according to claim 17, in which the sodium lauryl sulfate is present in a concentration of 4% to 6%.

25. The bioadhesive therapeutic system according to claim 17, further comprising corn starch.

26. The bioadhesive therapeutic system according to claim 17, further comprising between 0.1% and 1% of a monohydrate sugar.

27. The bioadhesive therapeutic system according to claim 26, in which the monohydrate sugar is lactose monohydrate.

28. The bioadhesive therapeutic system according to claim 17, further comprising magnesium stearate.

* * * * *